United States Patent [19]

Knifton et al.

[11] 4,016,194

[45] Apr. 5, 1977

[54] PREPARATIVE PROCESS FOR PREPARING PHENYLENEDIACETATE DIESTERS

[75] Inventors: John F. Knifton, Poughquag; Robert M. Suggitt, Wappingers Falls, both of N.Y.

[73] Assignee: Texaco Inc., New York, N.Y.

[22] Filed: Sept. 24, 1975

[21] Appl. No.: 616,227

[52] U.S. Cl. .................. 260/475 SC; 260/465 D; 260/473 R
[51] Int. Cl.² ......................................... C07C 69/76
[58] Field of Search ...... 260/475 SC, 473 R, 465 D

[56] References Cited

UNITED STATES PATENTS

| 3,437,676 | 4/1969 | Kutepow et al. | 260/468 |
| 3,636,082 | 1/1972 | Knowles | 260/475 R |

OTHER PUBLICATIONS

Falbe, Carbon Monoxide in Organic Synthesis pp. 118–120, (1970).
Heck, J.A.C.S., 85, pp. 2013–2014 (1963).

*Primary Examiner*—Jane S. Myers
*Attorney, Agent, or Firm*—Thomas H. Whaley; Carl G. Ries; Bernard Marlowe

[57] ABSTRACT

This invention relates to the catalytic carbonylation of α,α'-dihaloxylenes to phenylenediacetate diesters by the catalytic insertion of carbon monoxide into the carbon-halogen bonds of said α,α'-dihaloxylenes in the presence of alkanols. The catalysts used in this novel process are two component homogeneous ligand-stabilized palladium(II) and nickel(II) halide complexes wherein said stabilizing ligands each contain at least one Group VB or VIB donor atom such as phosphorus, which is bonded to one or more aromatic and/or aliphatic radicals.

12 Claims, No Drawings

PREPARATIVE PROCESS FOR PREPARING PHENYLENEDIACETATE DIESTERS

SUMMARY OF THE INVENTION

This invention concerns a process for preparing phenylenediacetate diesters by the catalyzed carbonylation of $\alpha,\alpha'$-dihaloxylenes in the presence of alkanols containing 1 to 8 carbon atoms, using two-component homogeneous Group VIII metal halide catalysts under relatively moderate pressures of carbon monoxide and relatively mild temperatures.

More specifically, this invention relates to the preparation of phenylenediacetate diesters by the insertion of carbon monoxide into the carbon-chlorine bonds of $\alpha,\alpha'$-dichloroxylenes, in the presence of alkanols containing 1 to 8 carbon atoms using homogeneous ligand-stabilized palladium(II) or nickel(II) chloride catalysts wherein said ligands each contain at least one Group VB or VIB donor atom such as phosphorous which is bonded to one or more aromatic and/or aliphatic radicals.

BACKGROUND OF THE INVENTION

The diester aromatic products of this invention are confined to the scope of the generic formula shown below:

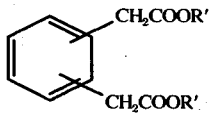

wherein R' is an alkyl radical of 1 to 8 carbon atoms and the two acetate ester groups can be meta, ortho or para to each other.

The diester products of this invention are produced by the overall reaction shown below in which the preferred dimethyl para or ortho-phenylenediacetate esters are the preferred product.

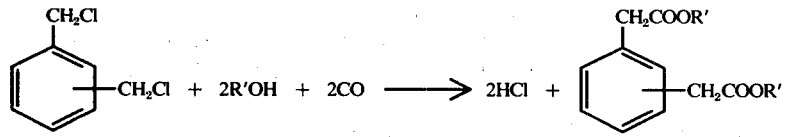

The preferred dimethyl p-phenylenediacetate is useful as a monomer for polyester copolymers as well as other polymeric formulations.

The closest prior art for preparing the preferred product, dimethyl p-phenylenediacetate, is believed to be reported by R. F. Heck and D. S. Breslow in J. Amer. Chem. Soc., 85, 2779 (1963), who disclose a 32% yield of p-phenylenediacetic acid using near stoichiometric amounts of a cobalt carbonyl catalyst. Applicants have found that using the same dihaloxylene starting materials but $PdCl_2(PPh_3)_2$ as the homogeneous catalyst up to 56% yield of product is formed at initial dihalide to palladium mole ratios of 50 or higher. Quite unexpectedly good yields are obtained under non-forcing, low temperature and pressure conditions using the 2-component catalysts such as $PdCl_2(PPh_3)_2$ in the absence of Group IV metal halide co-catalysts such as $SnCl_2$ which are needed to achieve carbonylation of vinylic halides*.

*Ser. No. 372,899

PROCESS DESCRIPTION

While the novel carbonylation process of this invention is not limited to xylene dihalides, such as $\alpha,\alpha'$-dichloro-p-xylene, as starting material (or substrate), for the sake of simplicity, the following description will be limited as though said $\alpha,\alpha'$-dichlorinated xylene is the substrate material employed and the phenylenediacetate esters are the major product formed.

In the practice of this invention, $\alpha,\alpha'$-dihaloxylenes, preferably the $\alpha,\alpha'$-dichloro-p-xylene, may be converted to the corresponding diesters in good yield at relatively mild parameters of temperatures and pressures by the process of:

a. admixing each mole of said $\alpha,\alpha'$-dichloroxylene to be carbonylated with at least two molar equivalents of an alcohol co-reactant containing 1 to 8 carbon atoms, such as methanol, and with a catalytic amount of a homogeneous ligand-stabilized palladium(II) or nickel-(II) halide catalyst wherein said stabilizing ligands each contain at least one Group VB or VIB donor atom bonded to one or more aromatic and/or aliphatic radicals, such as in the palladium and nickel complexes $PdCl_2[P(C_6H_5)_3]_2$ and $NiCl_2[P(C_6H_5)_3]_2$;

b. optionally adding an alkali salt to the reaction mixture;

c. pressurizing said mixture to superatmospheric pressure with sufficient carbon monoxide to satisfy the stoichiometry of the diester reaction;

d. heating said pressurized reaction mixture until conversion of the $\alpha,\alpha'$-dichloro-p-xylene to said dimethyl p-phenylenediacetate ester takes place, and e. optionally isolating said diacetate ester contained therein.

In order to present the inventive concept in the greatest possible detail as to promote its understanding, the following supplementary disclosure is submitted:

A. Process Sequence and Variations. In general, the components of the aforementioned reaction mixture including optional alkali salt, alcohol co-reactant, $\alpha,\alpha'$-dihaloxylene substrate and catalyst may be added in any sequence as long as sufficiently good agitation is provided to assure the formation of a homogeneous mixture. For example, the following represent some variations insofar as the catalyst, sequence of CO and heating that may be made without departing from the inventive process. These modifications include:

1. The catalyst may be preformed and added to the reaction mixture, or
2. the catalyst may be formed in situ.

Optionally, a deoxygenated inert solvent may also be added to the reaction mixture consisting of the $\alpha,\alpha'$-dihaloxylene, alcohol coreactant and homogeneous ligand-stabilized palladium(II) or nickel(II) halide catalyst prior to the carbonylation step. The system may be pressurized to superatmospheric pressures with carbon monoxide prior to heating, or the reaction mixture may be heated to reaction temperature under autogeneous pressures, and then the pressure raised to the desired level with carbon monoxide. Reaction times may be selected empirically, or determined by monitoring samples withdrawn for analysis during the reaction.

B. Homogeneous Ligand-Stabilized Palladium(II) or Nickel(II) Catalyst — The homogeneous palladium or nickel catalyst of this invention consists of at least two components, (1) a palladium(II) or nickel(II) halide salt selected from the group consisting of palladium(II) chloride palladium(II) bromide, palladium(II) iodide, nickel(II) chloride, nickel(II) bromide and nickel(II) iodide, complexed with (2) one or more complexing ligands each containing at least one Group VB or VIB donor atom, such as nitrogen, phosphorus, arsenic or sulphur that is:

a. Bonded to one or more alkyl, aryl, cycloalkyl, aralkyl, alkaryl and aryloxy radicals each containing 1 to 12 carbon atoms.

b. Part of a heteroaryl structure.

c. An alkyl or aryl nitrile.

Illustrative of suitable Group VB or VIB donor ligands which may be used in combination with the catalytic metal halides, such as $PdCl_2$ and $NiCl_2$, as carbonylation catalysts for the novel catalyzed preparation of phenylenediacetate esters are: $As(C_6H_5)_3$, $P(CH_3)_2(C_6H_5)$, $P(p\text{-}CH_3\text{-}C_6H_4)_3$, $S(C_6H_5)_2$, $(C_{12}H_8N_2)$*, $P(p\text{-}Cl.C_6H_4)_3$, $P(o\text{-}CH_3O.C_6H_4)_3$, $P(p\text{-}CH_3O.C_6H_4)_3$, $C_6H_5CN$, $P(OC_6H_5)_3$, $P(C_6H_{11})_3$, $As(n\text{-}C_4H_9)_3$, $P[(p\text{-}CH_3.C_6H_4)(C_6H_5)_2]$, $(C_6H_5)_2P(CH_2)_2P(C_6H_5)_2$, $(C_6H_5)_2P(CH_2)P(C_6H_5)_2$ and $Sb(C_6H_5)_3$.

* $C_{12}H_8N_2 = 1,10$-phenanthroline.

The following complexes are among the many ligand-stabilized palladium(II) and nickel(II) halide complexes which can be used in the catalytic carbonylation of $\alpha,\alpha'$-dihaloxylene substrates to the corresponding phenylenediacetate esters:

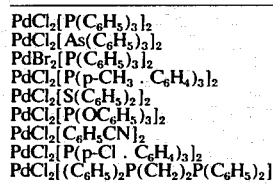
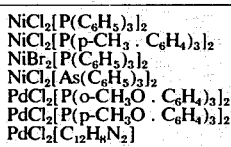

$PdCl_2[P(C_6H_5)_3]_2$
$PdCl_2[As(C_6H_5)_3]_2$
$PdBr_2[P(C_6H_5)_3]_2$
$PdCl_2[P(p\text{-}CH_3 \cdot C_6H_4)_3]_2$
$PdCl_2[S(C_6H_5)_2]_2$
$PdCl_2[P(OC_6H_5)_3]_2$
$PdCl_2[C_6H_5CN]_2$
$PdCl_2[P(p\text{-}Cl \cdot C_6H_4)_3]_2$
$PdCl_2[(C_6H_5)_2P(CH_2)_2P(C_6H_5)_2]$ $NiCl_2[P(C_6H_5)_3]_2$
$NiCl_2[P(p\text{-}CH_3 \cdot C_6H_4)_3]_2$
$NiBr_2[P(C_6H_5)_3]_2$
$NiCl_2[As(C_6H_5)_3]_2$
$PdCl_2[P(o\text{-}CH_3O \cdot C_6H_4)_3]_2$
$PdCl_2[P(p\text{-}CH_3O \cdot C_6H_4)_3]_2$
$PdCl_2[C_{12}H_8N_2]$ In all cases the Group VB* or VIB* donor ligand, typified by triphenylphosphine, may be used in excess of the amount required by stoichiometry for complex formation.

* As defined by F. A. Cotton & G. Wilkinson; Advanced Inorganic Chemistry, Interstate Publishers, 1962 Ed.

C. Ratio of Palladium Catalyst to $\alpha,\alpha'$-Dihaloxylene Substrate — Experimental work indicates that a mole ratio of up to $10^4$ moles of $\alpha,\alpha'$-dihaloxylene substrate per mole of palladium catalyst can be employed in most instances where the $\alpha,\alpha'$-dihaloxylene substrate is typified by $\alpha,\alpha'$-dichloroxylene. Much lower ratios (e.g. 25 mole of dihalide per mole of palladium or nickel halide) are not harmful but are economically unattractive.

D. Temperature and Pressure required for Ester Formation — The temperature and pressure ranges which can be employed for ester formation are variable dependent upon other experimental factors including the nature and concentration of the substrate employed, the concentration and the particular choice of catalyst and the addition of alkali salt, among other things.

Again using $\alpha,\alpha'$-dichloroxylene as a typical substrate and $PdCl_2[P(C_6H_5)_3]_2$ as a representative catalyst, the range of operability is from about 20° C to at least 150° C when superatmospheric pressures of about 50 to 4000 psig or higher are employed. Table II provides the supporting experimental data.

E. Reaction Times Required — As previously indicated in the analogous discussion on temperatures and pressures required in the reaction, experimental variables are important in arriving at reaction times. Generally substantial conversions (70% or higher) of the substrates to the ester can almost always be accomplished within 48 hours with 6 to 24 hours representing the more usual reaction time interval.

F. Dihaloxylene Substrate — As used throughout this disclosure, this term refers to a group of halogenated substrates containing the $\alpha,\alpha'$-dihaloxylene structure in which the carbon-halogen bonds of the halomethylene substituents are available for CO insertion. Suitable $\alpha,\alpha'$-dihaloxylenes include $\alpha,\alpha'$-dichloro, dibromo and diiodoxylenes, and mixed halogenated xylenes. The halomethyl groups may be ortho, meta or para to one another, as in the case of $\alpha,\alpha'$-dichloro-o-xylene, $\alpha,\alpha'$-dichloro-p-xylene and $\alpha,\alpha'$-dichloro-m-xylene, and other substituent groups such as alkyl, aryl, alkoxy, acetoxy, nitrile and halogen functions may also be present in the substrate molecule. Examples of suitable substituted dihaloxylenes include 3,6-bis(chloromethyl) durene, 3,4-bis(chloromethyl)cyclohexylbenzene, 3,4-bis(chloromethyl)anisole, 3,4-bis(chloromethyl)toluene, 3,5-bis(chloromethyl)chlorobenzene, 3,5-bis(chloromethyl)acetophenone, 3,6-bis(chloromethyl)acetophenone, and 3,5-bis(chloromethyl)benzonitrile, and mixtures of each of these thereof.

G. Alkali Salt — The alkali salt that may optionally be added to the carbonylation mixture of $\alpha,\alpha'$-dihaloxylene substrate, homogeneous palladium or nickel halide catalyst, and alcohol coreactant may be selected from the group including alkali hydroxides, such as sodium hydroxide and potassium hydroxide, alkali alkoxides such as sodium methoxide, and alkali phenoxides such as potassium phenoxide, and soluble alkali salts such as sodium acetate and potassium propionate. A preferred alkali salt for the synthesis of phenylenediacetate esters under mild conditions is sodium methoxide.

H. Alcohol Co-Reactant — If it is desired to prepare ester products, an alcohol co-reactant should be present in the reaction mixture with the $\alpha,\alpha'$-dihaloxylene substrate, carbon monoxide and catalyst in sufficient quantity to satisfy the stoichiometry of the reaction. The alcohol may be a monohydric primary or secondary alkanol of up to 8 carbon atoms. Suitable examples include methanol, ethanol, isopropanol, 1-hexanol, 2-pentanol, 1-butanol, 3-butanol and 2-ethylhexanol. Alternatively the alcohol coreactant may be a polyol such as ethylene glycol, propylene glycol, glycerine and tetraethylene glycol.

I. Carbon monoxide Environment — Insofar as can be determined, the best selectivities and conversions of unsaturated aliphatic halide to unsaturated aliphatic ester can be obtained within a reasonable reaction time by using a substantially carbon monoxide gaseous atmosphere. However, particularly in continuous operation, the carbon monoxide may be used in conjunction with from about 0 to 30% by volume of one or more inert gases such as nitrogen, argon, neon and the like without experiencing a substantial decrease in yield and selectivity.

J. Inert Solvents — The novel reaction may be conveniently run in the presence of an inert diluent. A variety of inert solvents can be used, including aromatics such as benzene, toluene and xylenes, halogenated aromatics including o-dichlorobenzene and chloronaphthalene, ethers such as dimethoxyethane and p-dioxane, halogenated paraffins including methylene chloride, and ketones such as acetone, methyl ethyl ketone and methyl isopropyl ketone.

K. Conversion — Conversion as defined herein is the efficiency in converting the $\alpha,\alpha'$-dihaloxylene substrate to non-halogenated products. Conversion is expressed as a percentile and is calculated herein by dividing the amount of $\alpha,\alpha'$-dihaloxylene substrate consumed during carbonylation* by the amount of $\alpha,\alpha'$-dihaloxylene charged to the reactor and multiplying the quotient by 100.

*Carbonylation as used throughout this disclosure refers to the insertion of carbon monoxide into the carbon-halogen bonds of the $\alpha,\alpha'$-dihaloxylene substrate, and is accompanied by hydrogen halide displacement.

L. Yield — as defined herein is the efficiency in catalyzing the desired carbonylation reaction relative to other undesired reactions. In this instance carbonylation of the $\alpha,\alpha'$-dihaloxylenes to phenylenediacetate esters is the desired reaction. Yield is usually expressed as a percentile, and is calculated by determining the amount of diester formed, divided by the amount of $\alpha,\alpha'$-dihaloxylene charged, and multiplying the quotient obtained by 100.

M. By-Products — As far as can be determined, without limiting the invention or its novelty, the essence of the inventive process is carbonylation involving carbon monoxide insertion into the carbon-halogen bonds of the $\alpha,\alpha'$-dihaloxylene substrate accompanied by hydrogen halide displacement. Consequently, both phenylenediacetate and monoacetate esters may be formed during carbonylation, the relative amounts of the two esters is illustrated in Table I for a variety of catalysts.

Unless otherwise stated, all parts are by weight, all temperatures in degrees centigrade and all pressures in pounds per square inch gauge (psig).

EXAMPLE 1

Preparation of Dimethyl p-Phenylenediacetate

Part A — To an appropriately sized, glass lined reactor provided with agitation, heating, cooling and pressurizing means, is charged with a degassed sample of methanol (100 ml), 3.50g (20 mmole) of $\alpha,\alpha'$-dichloro-p-xylene, 8.16g (60 mmoles) of sodium acetate and 0.28g (0.4 mmole) of bis(triphenylphosphine)palladium(II) chloride. The mixture is agitated to solubilize most of the solids, the reactor flushed with carbon monoxide, pressurized up to about 200 psig with CO and heated to 80° C for 48 hours. After cooling, a clear yellow product solution is recovered and analyzed by glpc. Dimethyl-p-phenylenediacetate is isolated as a pure product giving a yield of 52%. The remainder is by-products such as the monoacetate.

Part B — The procedure of Example 1, Part A is followed almost identically except that the catalyst $PdCl_2[P(C_6H_5)_3]_2$—$SnCl_2$ is employed as the catalyst. After heating to 80° for 48 hours under CO pressure with the $SnCl_2$ enriched catalyst, cooling, working up, etc., the yield of dimethyl p-phenylenediacetate is <1%.

Part C — The procedure of Example 1, Part B is followed except that the $SnCl_2$ enriched reaction mixture is heated to 120° C at 2000 psig for 6 hours. At the end of this time a yield of <1% of dimethyl p-phenylenediacetate product is obtained.

A comparison of Example 1, Parts A, B and C indicates that the addition of Group IVB halide salts, such as tin(II) chloride, to the reaction mixture significantly decreases the yield of desired phenylenediacetate diester product. The results of experiments 1B and C should be compared with the carbonylation of vinylic halides using similar ligand-stabilized palladium(II) halide catalysts in combination with tin(II) halide cocatalysts as set forth in Ser. No. 372,899, where good yields of acrylate ester are only obtained in the presence of excess Group IVB metal halide cocatalyst.

EXAMPLES 2 to 10

Preparation of Dimethyl p-Phenylenediacetate Catalyzed by Various Palladium and Nickel Complexes Using the process conditions and $\alpha,\alpha'$-dichloro-p-xylene substrate of Example 1, Part A, the following palladium and nickel complexes were substituted for bis(triphenylphosphine) palladium(II) chloride on a mole per mole basis. The results summarized in Table I show that under the selected carbonylation conditions 1. A variety of ligand-stabilized palladium(II) halide and nickel(II) halide complexes are suitable homogeneous catalysts for the synthesis of p-phenyldiacetate esters.

2. Simple palladium salts such as $PdCl_2$ do not give significant yields of diester even under more forcing conditions (Example 8).

3. Analogous ligand-stabilized platinum(II) halide salts such as $PtCl_2(As(C_6H_5)_3)_2$ are not effective under the selected carbonylation conditions (Example 10).

4. In contrast to the cobalt carbonyl catalysts of the prior art, the exemplified ligand-stabilized nickel and palladium catalysts give reasonable yields of diester even at initial $[C_6H_4(CH_2Cl)_2]/[Pd]$ ratios of fifty or more.

EXAMPLES 11 to 18

Preparation of Dimethyl p-Phenylenediacetate Catalyzed by Various Palladium and Nickel Complexes Using the process conditions and $\alpha,\alpha'$-dichloro-p-xylene substrate of Example 1, Part A, the following palladium and nickel complexes were substituted for bis(triphenylphosphine) palladium(II) chloride on a mole per mole basis. Each catalyst complex showed satisfactory performance for the synthesis of dimethyl p-phenylenediacetate.

| EXAMPLE | CATALYST COMPOSITION |
| --- | --- |
| 11 | $PdCl_2[P(p-CH_3O . C_6H_4)_3]_2$ |
| 12 | $PdCl_2[P(o-CH_3O . C_6H_4)_3]_2$ |
| 13 | $PdCl_2[P(p-Cl . C_6H_4)_3]_2$ |
| 14 | $PdCl_2[(C_6H_5)_2P(CH_2)_2P(C_6H_5)_2]$ |
| 15 | $NiCl_2[P(p-CH_3 . C_6H_4)_3]_2$ |
| 16 | $NiCl_2[As(C_6H_5)_3]_2$ |
| 17 | $NiBr_2[P(C_6H_5)_3]_2$ |
| 18 | $PdBr_2[P(C_6H_5)_3]_2$ |

TABLE I

PREPARATION OF DIMETHYL p-PHENYLENEDIACETATE CATALYZED BY VARIOUS PALLADIUM AND NICKEL COMPLEXES[a]

| EXAMPLE | CATALYST COMPOSITION | αα'-DICHLORO-p-XYLENE CONVERTION (%) | YIELD OF CARBONYLATED MONOACETATE ESTER[b] | YIELD OF CARBONYLATED PRODUCTS (MOLE %) DIACETATE ESTER[c] |
|---|---|---|---|---|
| 2 | $PdCl_2(As(C_6H_5)_3)_2$ | >95 | 40 | 27 |
| 3 | $PdCl_2(P(p\text{-}CH_3 \cdot C_6H_4)_3)_2$ | >95 | 33 | 50 |
| 4 | $PdCl_2(S(C_6H_5)_2)_2$ | >95 | 45 | 28 |
| 5 | $PdCl_2(P(OC_6H_5)_3)_2$ | 83 | 43 | 38 |
| 6 | $PdCl_2(C_6H_5CN)_2$ | >95 | 47 | 40 |
| 7 | $PdCl_2(C_{12}H_8N_2)$[d] | >95 | 43 | 36 |
| 8 | $PdCl_2$ | 100 | <1 | <1 |
| 9 | $NiCl_2(P(C_6H_5)_3)_2$ | >95 | 37 | 31 |
| 10 | $PtCl_2(As(C_6H_5)_3)_2$ | 3 | <1 | <1 |

[a]Run Conditions: $[C_6H_4(CH_2Cl)_2]/[Pd]$=50; $[Pd]$=0.004M; Solvent, Methanol, Excess NaOMe, 350 psig CO, 80° C, 12–24hr.
[b]Monoacetate Ester, a mixture of methyl p-(chloromethyl)phenyleneacetate and Methyl p-(methoxymethyl)-phenyleneacetate
[c]Diacetate Ester, Dimethyl p-Phenylenediacetate

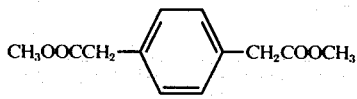

[d]$C_{12}H_8N_2$ = 1,10-Phenanthroline.

EXAMPLE 19

Preparation of Dimethyl O-Phenylenediacetate

Using the procedure, equipment, proportions and reaction parameters employed in Example 1, Part A, α,α'-dichloro-o-xylene is selectively carbonylated to dimethyl o-phenylenediacetate in the presence of the homogeneous bis(triphenylphosphine)palladium(II) chloride catalyst. At the end of the reaction time, the pressurized reactor is cooled, vented, and the liquid product analyzed by glpc. Yield of dimethyl o-phenylenediacetate was calculated to be 69 mole %.

EXAMPLE 20

Preparation of Dimethyl 2,3,5,6-Tetramethylphenylene-1,4-Diacetate

Part A — In this example, the procedure, equipment, proportions and reaction parameters of Example 1, Part A, are used, but in this case 3,6-bis(chloromethyl)durene is selectively carbonylated to dimethyl 2,3,5,6-tetramethylphenyl-1,4-diacetate. After work up the acetate esters are calculated to be formed in > 55 mole % yield.

Part B — The procedure of Example 20, Part A is followed except that the sodium acetate is replaced by potassium hydroxide and by sodium acetate in a mole per mole basis. In both cases dimethyl 2,3,5,6-tetramethylphenyl-1,4-diacetate is a major product.

EXAMPLES 21 to 24

Synthesis of Diethyl p-Phenylenediacetate and its Homologs

In these Examples the procedure set forth in Example 1, Part A is followed using almost duplicate conditions and reactants except that the designated higher alcohols are employed instead of methanol on a mole per mole basis. The corresponding p-phenylenediacetate esters are obtained in good yields.

| EXAMPLES | ALCOHOL EMPLOYED |
|---|---|
| 21 | Ethanol |
| 22 | Isopropanol |
| 23 | 1-Butanol |
| 24 | 2-Ethylhexanol |

EXAMPLES 25 to 30

Preparation of Dimethyl p-Phenylenediacetate Under Various Experimental Conditions In these Examples, using the operating procedure, catalyst and alcohol coreactant of Example 1, Part A, dimethyl p-phenylenediacetate is prepared from α,α'-dichloro-p-xylene over a wide range of experimental conditions (See Table II) as follows:

1. Reaction temperature of 20° to 150° C.
2. Pressures of CO from 100 to 4000 psig.
3. Reaction time of 6 to 48 hours.
4. Added alkali salt, sodium methoxide, and without added alkali.
5. Benzene as an added inert solvent.

TABLE II

PREPARATION OF DIMETHYL p-PHENYLENEDIACETATE UNDER VARIOUS EXPERIMENTAL CONDITIONS[a]

| EXAMPLE | REACTION TEMPERATURE (°C) | PRESSURE CO(PSIG) | REACTION TIME (HR.) | α,α'-DICHLORO-p-XYLENE CONVERSION (%) | YIELD OF DIMETHYL p-PHENYLENEDIACETATE (MOLE %) |
|---|---|---|---|---|---|
| 25 | 70 | 4000 | 12 | >95 | 55 |
| 26 | 80 | 350 | 24 | >95 | 52 |
| 27 | 80 | 100 | 24 | >95 | 56 |
| 28 | 20 | 2000 | 48 | 62 | <5 |
| 29 | 120 | 2000 | 6 | 40 | 5 |

TABLE II-continued

PREPARATION OF DIMETHYL p-PHENYLENEDIACETATE UNDER VARIOUS EXPERIMENTAL CONDITIONS[a]

| EXAMPLE | REACTION TEMPERATURE (° C) | PRESSURE CO(PSIG) | REACTION TIME (HR.) | α,α'-DICHLORO-p-XYLENE CONVERSION (%) | YIELD OF DIMETHYL p-PHENYLENEDIACETATE |
|---|---|---|---|---|---|
| 30 | 150 | 2000 | 24[b] | >95 | 15 |

[a]Run Conditions: $[C_6H_4(CH_2Cl)_2]/[Pd] = 50$; $[Pd] = 0.004$ M; Solvent, Benzene/Methanol 1:1 (V/V); Excess NaOMe
[b]No NaOMe added.

As the numerous examples and preceding discussion have documented, numerous advantages accrue from the practice of this invention, both in its compositional aspect and its process aspects.

For example, a relatively large group of ligand-stabilized palladium(II) and nickel(II) halide catalysts are provided where were heretofore not known to be useful as catalysts for the conversion of α,α'-dihaloxylenes to dialkyl phenyleneacetate esters. These catalytic compositions offer the further advantage of being readily available by well known preparative procedures, and in contrast to the cobalt carbonyl catalysts of the prior art, they have conversion efficacies even at substrate to catalyst molar ratios as high as $10^4$ to 1 molar ratios, dependent upon the choice of dihaloxylene substrate, and the particular catalyst employed.

In its process aspect, this invention provides an improved process for preparing the phenylenediacetate esters in improved yields free from undesired contaminants. In addition, while reaction times are not rapid, since the process utilizes mild temperatures and moderate pressures, it lends itself to either batch or continuous operation, employing standard equipment.

A further advantage of the instant invention is that, while in some respects reaction conditions are critical to success, in other respects the process offers flexibility. That is, numerous modifications and changes can be made in the choice of catalysts and dihalide substrates, without departing from the inventive concept. The metes and bounds of this invention can best be determined by reading the claims which follow in light of the preceding specification.

What is claimed is:

1. A process for converting α,α'-dihaloxylene substrates selected from the group consisting of α,α'-dichloro-p-xylene, α,α'-dichloro-O-xylene, α,α'-dichloro-m-xylene, α,α'-dibromo-p-xylene, α,α'-dibromo-O-xylene, α,α'-dibromo-m-xylene, α,α'-diiodo-p-xylene, α,α'-diiodo-o-xylene, α,α'-diiodo-m-xylene, 3,6-bis(chloromethyl) durene, 3,4-bis(chloromethyl)-cyclohexylbenzene, 3,4-bis(chloromethyl)anisole, 3,4-bis(chloromethyl)toluene, 3,5-bis(chloromethyl)chlorobenzene, 3,5-bis(chloromethyl) acetophenone, 3,6-bis(chloromethyl)acetophenone, 3,5-bis(chloromethyl)benzonitrile, and mixtures of each of these thereof, to dialkyl phenylenediacetate esters in good yields and conversions by a process of:

a. admixing each mole of said α,α'-dihaloxylene substrate to be converted to said phenylenediacetate ester with at least a catalytic amount of a homogeneous ligand-stabilized palladium(II) or nickel(II) halide catalyst consisting of two components, a palladium(II) or nickel(II) halide salt and a Group VB or VIB stabilizing ligand, said 2-component catalyst being selected from the group consisting of:

$PdCl_2[P(OC_6H_5)_3]_2$
$PdCl_2[P(p-CH_3 \cdot C_6H_4)_3]_2$
$PdCl_2[P(p-Cl \cdot C_6H_4)_3]_2$
$PdCl_2[(C_6H_5)_2P(CH_2)_2P(C_6H_5)_2]$
$PdCl_2[P(C_6H_5)_3]_2$
$PdCl_2[S(C_6H_5)_3]_2$
$PdCl_2[C_6H_5CN]_2$
$NiCl_2[P(C_6H_5)_3]_2$
$PdCl_2[As(C_6H_5)_3]_2$ $PdCl_2[C_{12}H_8N_2]$
$PdCl_2[P(p-CH_3OC_6H_4)_3]_2$ $NiCl_2[P(p-CH_3C_6H_4)_3]_2$
$NiCl_2[As(C_6H_5)_3]_2$
$NiBr_2[P(C_6H_5)_3]_2$
$PdBr_2[P(C_6H_5)_3]_2$ and at least two molar equivalents of an alcohol co-reactant containing from 1 to 8 carbon atoms, to form a reaction mixture, b. pressurizing said reaction mixture to superatmospheric pressures ranging from about 50 to 4000 psig with more than a sufficient amount of carbon monoxide to satisfy the stoichiometry of the diester reaction;

c. heating said pressurized reaction mixture from 20° to about 120° C until conversion of the α,α'-dihalides of xylene to said dialkyl phenylenediacetate takes place, and d. isolating said phenyldiacetates contained therein.

2. The process of claim 1 wherein an alkali salt is added to the reaction mixture before the carbonylation reaction is started.

3. The process of claim 2 wherein the added alkali salt is selected from the group consisting of sodium acetate, potassium methoxide, sodium methoxide, sodium hydroxide and potassium hydroxide.

4. The process of claim 1 wherein said homogeneous catalyst is prepared in situ by adding as separate components the palladium(II) or nickel(II) halide and the Group VB or VIB stabilizing ligands.

5. The process of claim 1 wherein the catalyst is added to the reaction mixture preformed.

6. The process of claim 1 wherein the reaction mixture contains an inert solvent.

7. The process of claim 6 wherein the inert solvent is selected from the group consisting of benzene, toluene and xylenes.

8. The process of claim 1 wherein α,α'-dichloro-p-xylene is the α,α'-dihaloxylene substrate, methanol is the alcohol coreactant, and the major phenylenediacetate diester product is dimethyl p-phenylenediacetate.

9. The process of claim 1 wherein α,α'-dichloro-o-xylene is the substrate, methanol is the alcohol coreactant and the major diester product is dimethyl o-phenylenediacetate.

10. The process of claim 1 wherein the alcohol coreactant is selected from the group including methanol, ethanol, isopropanol, 1-butanol and 2-ethylhexanol.

11. The process of claim 1 wherein the α,α'-dihaloxylene substrate is a substituted α,α'-dihaloxylene.

12. The process of claim 11 wherein the α,α'-dihaloxylene substrate is 3,6-bis(chloromethyl)durene.

* * * * *